(12) United States Patent
Brenek et al.

(10) Patent No.: US 9,573,959 B2
(45) Date of Patent: Feb. 21, 2017

(54) METHODS FOR PREPARING SGLT2 INHIBITORS

(71) Applicant: MSD International GMBH, Lucerne (CH)

(72) Inventors: Steven J. Brenek, New York, NY (US); Stephane Caron, New York, NY (US); Jade D. Nelson, New York, NY (US); Mark E. Webster, New York, NY (US); Rodney Matthew Weekly, New York, NY (US)

(73) Assignee: MSD International GMBH, Luzern (CH)

( * ) Notice: Subject to any disclaimer, the term of this patent is extended or adjusted under 35 U.S.C. 154(b) by 0 days.

(21) Appl. No.: 14/777,560

(22) PCT Filed: Mar. 10, 2014

(86) PCT No.: PCT/US2014/022243
§ 371 (c)(1),
(2) Date: Sep. 16, 2015

(87) PCT Pub. No.: WO2014/159151
PCT Pub. Date: Oct. 2, 2014

(65) Prior Publication Data
US 2016/0046646 A1    Feb. 18, 2016

Related U.S. Application Data

(60) Provisional application No. 61/912,252, filed on Dec. 5, 2013, provisional application No. 61/887,504, filed on Oct. 7, 2013, provisional application No. 61/783,128, filed on Mar. 14, 2013.

(51) Int. Cl.
C07D 493/08    (2006.01)
C07D 317/26    (2006.01)
C07D 317/42    (2006.01)

(52) U.S. Cl.
CPC ......... *C07D 493/08* (2013.01); *C07D 317/26* (2013.01); *C07D 317/42* (2013.01)

(58) Field of Classification Search
None
See application file for complete search history.

(56) References Cited

U.S. PATENT DOCUMENTS

| | | | |
|---|---|---|---|
| 3,183,247 A | 5/1965 | Kiss et al. | |
| 6,414,126 B1 | 7/2002 | Ellsworth et al. | |
| 6,515,117 B2 | 2/2003 | Ellsworth et al. | |
| 6,936,590 B2 | 8/2005 | Washburn et al. | |
| 7,101,856 B2 | 9/2006 | Glombik et al. | |
| 7,169,761 B2 | 1/2007 | Tomiyama et al. | |
| 7,202,350 B2 | 4/2007 | Imamura et al. | |
| 7,851,502 B2 | 12/2010 | Bindra et al. | |
| 7,919,598 B2 | 4/2011 | Gougoutas et al. | |
| 7,943,582 B2 | 5/2011 | Nomura et al. | |
| 7,943,788 B2 | 5/2011 | Nomura et al. | |
| 8,080,580 B2 | 12/2011 | Mascitti et al. | |
| 8,221,786 B2 | 7/2012 | Bindra et al. | |
| 8,222,219 B2 | 7/2012 | Nomura et al. | |
| 8,361,972 B2 | 1/2013 | Bindra et al. | |
| 8,513,202 B2 | 8/2013 | Nomura et al. | |
| 8,669,380 B2 | 3/2014 | Mascitti | |
| 8,685,934 B2 | 4/2014 | Strumph et al. | |
| 8,716,251 B2 | 5/2014 | Bindra et al. | |
| 2002/0111315 A1 | 8/2002 | Washburn et al. | |
| 2002/0137903 A1 | 9/2002 | Ellsworth et al. | |
| 2004/0138439 A1 | 7/2004 | Deshpande et al. | |
| 2005/0176820 A1 | 8/2005 | Barrett et al. | |
| 2005/0209166 A1 | 9/2005 | Eckhardt et al. | |
| 2005/0233988 A1 | 10/2005 | Nomura et al. | |
| 2006/0025349 A1 | 2/2006 | Eckhardt et al. | |
| 2006/0035841 A1 | 2/2006 | Eckhardt et al. | |
| 2006/0063722 A1 | 3/2006 | Washburn et al. | |
| 2012/0184486 A1 | 7/2012 | Mascitti | |

FOREIGN PATENT DOCUMENTS

| | | | |
|---|---|---|---|
| WO | WO0127128 A1 | 4/2001 | |
| WO | WO0244192 A1 | 6/2002 | |
| WO | WO02088157 A1 | 11/2002 | |
| WO | WO03099836 A1 | 12/2003 | |
| WO | WO2004087727 A1 | 10/2004 | |
| WO | WO2005021566 A2 | 3/2005 | |
| WO | WO2005085267 A1 | 9/2005 | |
| WO | WO2006002912 A1 | 1/2006 | |
| WO | WO2006008038 A1 | 1/2006 | |
| WO | WO2006062224 A1 | 6/2006 | |
| WO | WO2007000445 A1 | 1/2007 | |
| WO | WO2007093610 A1 | 8/2007 | |
| WO | WO2008002824 A1 | 1/2008 | |
| WO | WO2010023594 A1 | 3/2010 | |
| WO | WO 2011051864 A1 * | 5/2011 | ........... C07D 493/08 |
| WO | WO2011051864 A1 | 5/2011 | |
| WO | WO2012019496 A1 | 2/2012 | |
| WO | WO2014159151 A1 | 10/2014 | |

OTHER PUBLICATIONS

Asano, T. et al., SGLT as a therapeutic target, Drugs of the Future, 2004, p. 461-466, vol. 29, No. 5.
Bowles, P. et al., Commericial Route Research and Development for SGLT2 Inhibitor Candidate Ertugliflozin, Organic Porcess Research & Development, 2014, p. 66-81, vol. 18.
International Searching Authority, TheInternational Search Report and The Written Opinion, Patent Cooperation Treaty, 2014, p. 1-7.

(Continued)

*Primary Examiner* — Golam M M Shameem
*Assistant Examiner* — Laura Daniel
(74) *Attorney, Agent, or Firm* — Janet E. Fair; Anna L. Cocuzzo

(57) ABSTRACT

This invention relates to methods for preparing a sodium-glucose transporter 2 (SGLT2) inhibitor, a cocrytalline SGLT2 and (S)-5-oxopyrrolidine-2-carboxylic acid (L-PGA) complex, and intermediates useful in the preparation of the said SGLT2 inhibitor.

7 Claims, 3 Drawing Sheets

(56) References Cited

OTHER PUBLICATIONS

Isaji, M., Sodium-glucose cotransporter inhibitors for diabetes, Current Opinion in Investigational Drugs, 2007, p. 285-292, vol. 8, No. 4.
Mascitti, V. et al., Discovery of a Clinical Candidate from the Structurally Unique Dioxa-bicyclo[3.2.1]octane Clas of Sodium-Dependent Glucose Cotransporter 2 Inhibitors, Journal of Medicinal Chemistry, 2011, p. 2952-2960, vol. 54.
Mascitti, V. et al., Stereoselective Synthesis of a Dioxa-bicyclo[3.2.1]octane SGLT2 Inhibitor, Organic Letters, 2010, p. 2940-2943, Vo. 12, No. 13.
Robinson, R. P. et al, C-Aryl glycoside inhibitors of SGLT2: Exploration of sugar modifications including C-5 spirocyclization, Bioorganic & Medicinal Chemistry Letters, 2010, p. 1569-1572, vol. 20.

\* cited by examiner

METHODS FOR PREPARING SGLT2 INHIBITORS

CROSS-REFERENCE TO RELATED APPLICATIONS

This application is a U.S. National Phase application under 35 U.S.C. §371 of PCT Application No. PCT/US14/022243, filed Mar. 10, 2014, which published as WO2014/159151 A1 on Oct. 2, 2014, and claims priority under 35 U.S.C. §365(b) from U.S. provisional patent application No. 61/783,128, filed Mar. 14, 2013; U.S. provisional patent application No. 61/887,504, filed Oct. 7, 2013 and U.S. provisional patent application No. 61/912,252, filed Dec. 5, 2012.

FIELD OF THE INVENTION

The present invention relates to methods for preparing certain sodium glucose cotransporter 2 (SGLT2) inhibitors and intermediates useful in the preparation of SGLT2 inhibitors.

BACKGROUND

Obesity is a significant health problem due to its serious medical complications that include co-morbidities such as hypertension, insulin resistance, diabetes, coronary artery disease and heart failure (collectively referred to as Metabolic Syndrome). Obesity and its related co-morbidities continue to cause rising health issues in the developed world and are beginning to affect the developing world as well. The negative health consequences of obesity make it the second leading cause of preventable death in the United States and impart a significant economic and psychosocial effect on society. See, McGinnis M, Foege W H., "Actual Causes of Death in the United States," *JAMA*, 270, 2207-12 (1993). There is a need to identify and develop new medications that treat and/or prevent obesity and its associated co-morbidities, in particular type II (type 2) diabetes.

More recently, sodium-glucose co-transport (SGLT) inhibitors, particularly SGLT2 inhibitors, have been shown to block the reabsorption of glucose from the renal filtrate in the glomerulus thereby inducing glucose excretion in the urine. As excess glucose is excreted, there is a decrease in blood glucose level, decreased hepatic storage of glucose, decreased insulin secretion and, subsequently, decreased carbohydrate conversion to fat and, ultimately, reduced accumulated fat. Selective inhibition of SGLT2 is expected to normalize plasma glucose by enhancing glucose excretion. Consequently, SGLT2 inhibitors provide an attractive means for the improvement of diabetic conditions without increasing body weight or the risk of hypoglycemia. See, Isaji, M., *Current Opinion Investigational Drugs*, 8(4), 285-292 (2007). For a general review of SGLT as a therapeutic target, see also Asano, T., et al., *Drugs of the Future*, 29(5), 461-466 (2004).

Representative examples of glycosides that have been shown to be useful for the treatment of NIDDM and obesity can be found in the following disclosures: U.S. Pat. Nos. 6,515,117; 6,414,126; 7,101,856; 7,169,761; and 7,202,350; U.S. Publication Nos. US2002/0111315; US2002/0137903; US2004/0138439; US2005/0233988; US2006/0025349; US2006/0035841; and US2006/0632722; and PCT Publication Nos. WO01/027128; WO02/044192; WO02/088157; WO03/099836; WO04/087727; WO05/021566; WO05/085267; WO06/008038; WO06/002912; WO06/062224; WO07/000445; WO07/093610; and WO08/002824.

Certain glycosides are genotoxic and impact a cell's genetic material such that they may be potentially mutagenic or carcinogenic. Genotoxic materials may be detected using standard assays such as the In Vitro Mammalian Cell Micronucleus Test (MNvit), Organization for Economic Co-Operation and Development (OECD) Draft Test Guideline (Draft TG) 487 (2007); In vitro Mammalian Chromosomal Aberration Test, OECD TG 473 (1997); Bacterial Reverse Mutation Test, OECD TG 471 (1997); Mammalian Erythrocyte Micronucleus Test, OECD TG 474 (1997); or the like. Consequently, there still exists a need for a more effective and safe therapeutic treatment and/or prevention of obesity and its associated co-morbidities, in particular, Type 2 diabetes and related disorders.

SUMMARY

The compound of Formula 1 has been found to act as a sodium-glucose cotransport (SGLT) inhibitor, in particular, SGLT2 inhibitor; therefore, may be used in the treatment of diseases mediated by such inhibition (e.g., diseases related to obesity, Type 2 diabetes, and obesity-related and diabetes-related co-morbidities).

One aspect of the invention is the intermediate compounds useful in the process to make the compound of Formula 1.

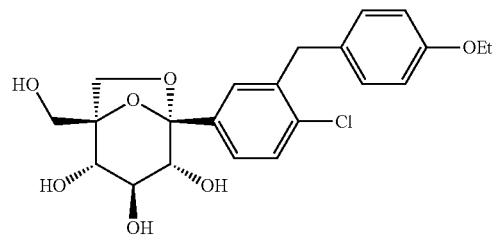

The said intermediate compounds are represented by Formulas 27, 28a/b, 29 and 30.

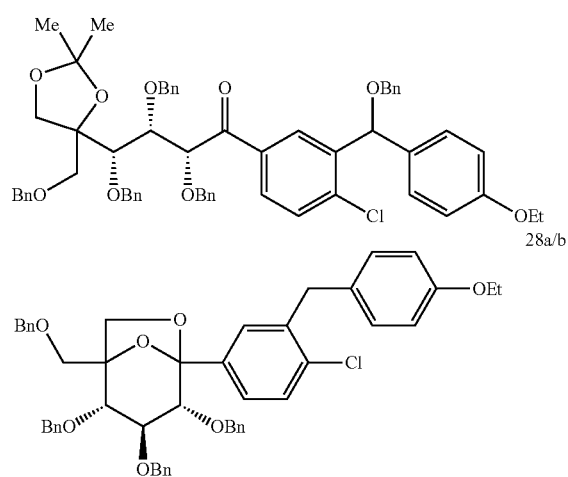

-continued

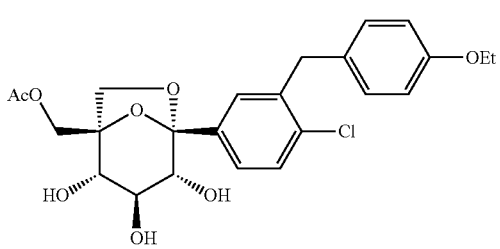

29

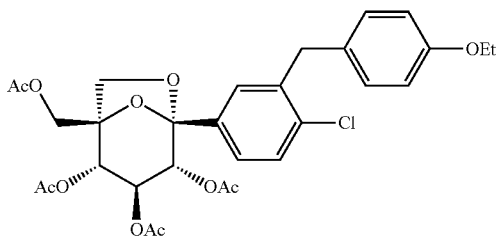

30

A further aspect of the invention provides methods for preparing the compound of Formula 1,

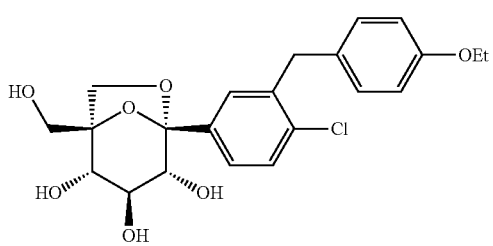

1 comprising treating the compound of Formula 28a/b,

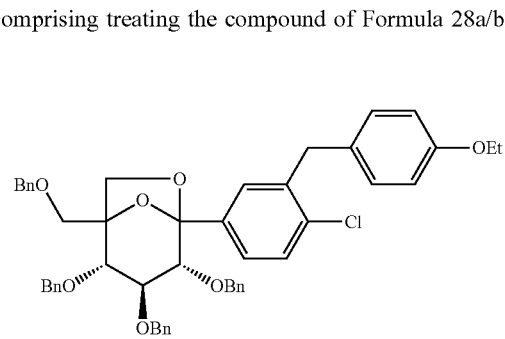

28a/b with a hydrogenolysis agent.

A further aspect of the present invention is a compound of Formula 29,

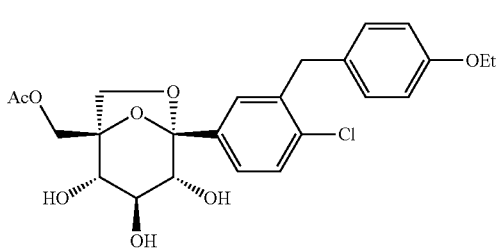

29 having a powder x-ray diffraction pattern comprising 2-theta values of (CuKα radiation, wavelength of 1.54056 Å) 5.8±0.2, 11.6±0.2, 16.0±0.2, 16.6±0.2, and 21.6±0.2.

Another aspect of the present invention is a compound of Formula 30,

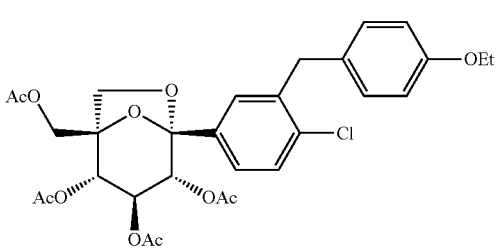

30 having a powder x-ray diffraction pattern comprising 2-theta values of (CuKα radiation, wavelength of 1.54056 Å) 5.7±0.2, 10.1±0.2, 11.5±0.2, 20.5±0.2, 21.4±0.2, and 24.6±0.2.

A further aspect of the present invention is a method for preparing a cocrystal compound of formula 1 (L-PGA),

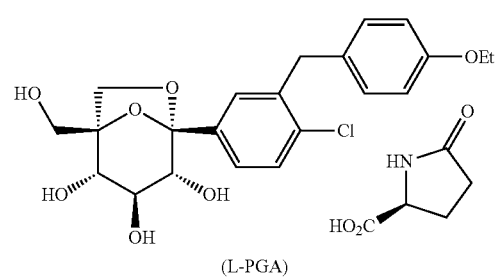

1

(L-PGA)

which includes treating the said compound of Formula 1 with L-pyroglutamic acid in a mixture of isopropanol and water to create a crystalline compound and reslurrying the crystalline compound with toluene or acetonitrile.

It is to be understood that both the foregoing general description and the following detailed description are exemplary and explanatory only and are not restrictive of the invention, as claimed.

DETAILED DESCRIPTION OF THE INVENTION

Figure 1:
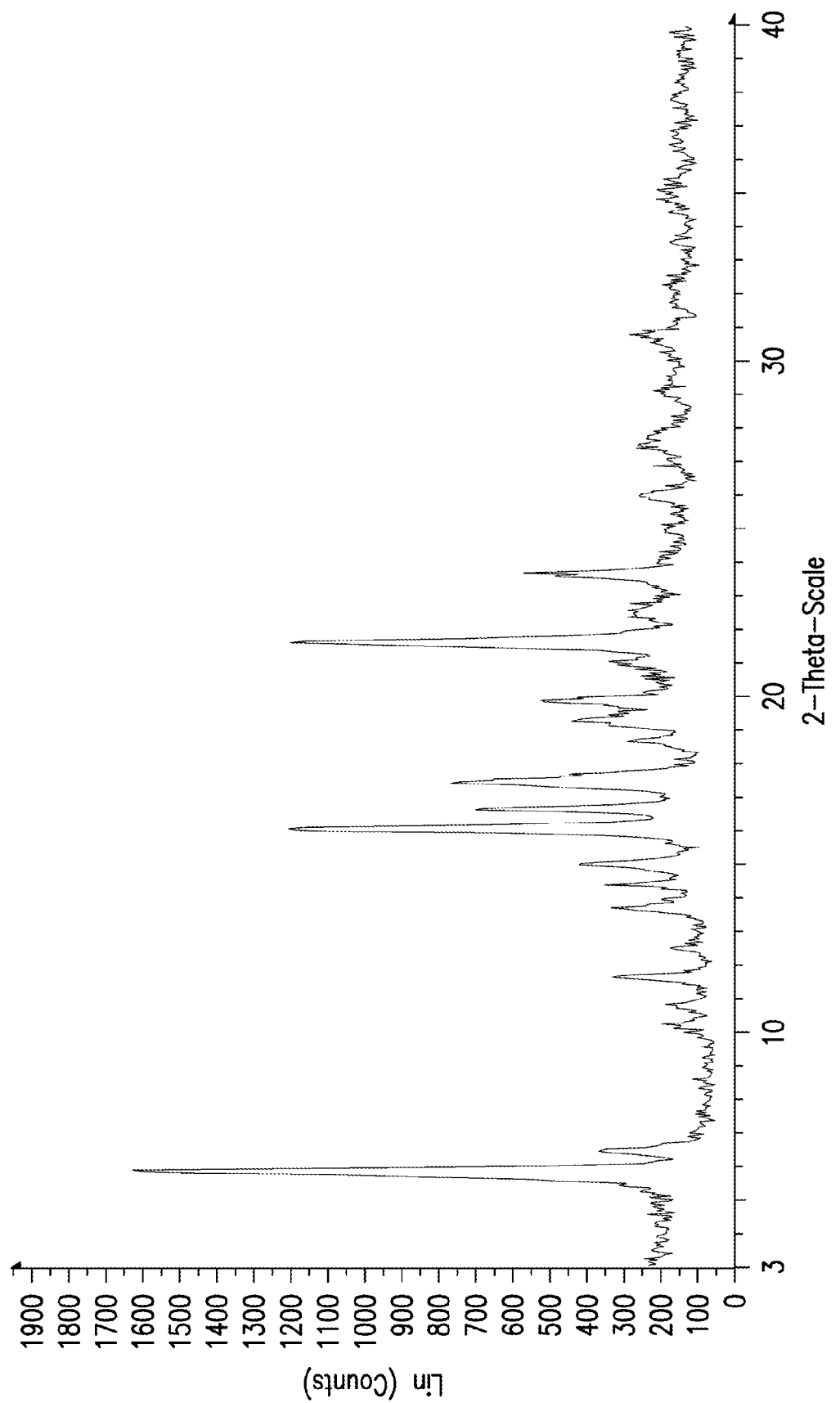
FIG. 1 represents an observed powder X-ray diffraction pattern for the compound of Formula 29.

The present invention may be understood even more readily by reference to the following detailed description of exemplary embodiments of the invention and the examples included therein.

Before the present compounds, compositions and methods are disclosed and described, it is to be understood that this invention is not limited to specific synthetic methods of making that may of course vary. It is also to be understood that the terminology used herein is for the purpose of describing particular embodiments only and is not intended to be limiting.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment.

The terms "modulated" or "modulating", or "modulate(s)", as used herein, unless otherwise indicated, refers to the inhibition of the sodium-glucose transporter (in particular, SGLT2).

The term "compounds of the invention" (unless specifically identified otherwise) refers to compounds described herein, and all pure and mixed stereoisomers (including diastereoisomers and enantiomers), tautomers and isotopically labeled compounds. Hydrates and solvates of the compounds of the invention are considered compositions of the present invention, wherein the compound is in association with water or solvent, respectively. The compounds may also exist in one or more crystalline states, i.e. as co-crystals, polymorphs, or they may exist as amorphous solids. All such forms are encompassed by the claims. The term "method of the invention" (unless specifically identified otherwise) refers to methods for preparing the compounds described herein and all pure and mixed stereoisomers.

The compounds of the invention contain asymmetric or chiral centers, and, therefore, exist in different stereoisomeric forms. Unless specified otherwise, it is intended that all stereoisomeric forms of the compounds of the invention as well as mixtures thereof, including racemic mixtures, form part of the present invention. In addition, the present invention embraces all geometric and positional isomers. For example, if a compound of the present invention incorporates a double bond or a fused ring, both the cis- and trans-forms, as well as mixtures, are embraced within the scope of the invention.

Diastereomeric mixtures can be separated into their individual diastereoisomers on the basis of their physical chemical differences by methods well known to those skilled in the art, such as by chromatography and/or fractional crystallization, distillation, sublimation. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the invention may be atropisomers (e.g., substituted biaryls) and are considered as part of this invention. Enantiomers can also be separated by use of a chiral HPLC (high pressure liquid chromatography) column.

It is also possible that the compounds of the invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the imidazole moiety where the proton may migrate between the two ring nitrogens. Valence tautomers include interconversions by reorganization of some of the bonding electrons. The equilibrium between closed and opened form of some intermediates (and/or mixtures of intermediates) is reminiscent of the process of mutarotation involving aldoses, known by those skilled in the art.

The present invention also embraces isotopically-labeled compounds of the invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine, iodine, and chlorine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{123}$I, $^{125}$I and $^{36}$Cl, respectively.

Certain isotopically-labeled compounds of the invention (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C, and $^{18}$F are useful for positron emission tomography (PET) studies to examine substrate occupancy. Isotopically labeled compounds of the invention can generally be prepared by following procedures analogous to those disclosed in the Schemes and/or in the Examples herein below, by substituting an isotopically labeled reagent for a non-isotopically labeled reagent.

Compounds of the invention are useful for preparing compounds to treat diseases, conditions and/or disorders modulated by the inhibition of the sodium-glucose transporters (in particular SGLT2). The compounds of the invention (including the compositions and processes used therein) may also be used in the manufacture of a medicament for the therapeutic applications described herein.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable dosage of the drug and to give the patient an elegant and easily handleable product.

The pharmaceutical compositions also include solvates and hydrates of the compounds of the invention. The term "solvate" refers to a molecular complex of a compound represented by Formula 27, Formula 28a/b, Formula 29, and Formula 30 (including pharmaceutically acceptable salts thereof) with one or more solvent molecules. Such solvent molecules are those commonly used in the pharmaceutical art, which are known to be innocuous to the recipient, e.g., water, ethanol, ethylene glycol, and the like, The term "hydrate" refers to the complex where the solvent molecule is water. The solvates and/or hydrates preferably exist in crystalline form. Other solvents may be used as intermediate solvates in the preparation of more desirable solvates, such as methanol, methyl t-butyl ether, ethyl acetate, methyl acetate, (S)-propylene glycol, (R)-propylene glycol, 1,4-butyne-diol, and the like. The crystalline forms may also exist as complexes with other innocuous small molecules, such as L-phenylalanine, L-proline, L-pyroglutamic acid and the like, as co-crystals or solvates or hydrates of the co-crystalline material. The solvates, hydrates and co-crystalline compounds may be prepared using procedures described in PCT Publication No. WO 08/002824, incorporated herein by reference, or other procedures well-known to those of skill in the art.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present invention further provides a method of treating diseases, conditions and/or disorders modulated by the inhibition of sodium-glucose transporters in an animal that includes administering to an animal in need of such treatment a therapeutically effective amount of a compound of the present invention or a pharmaceutical composition comprising an effective amount of a compound of the present invention and a pharmaceutically acceptable excipient, diluent, or carrier. The method is particularly useful for treating diseases, conditions and/or disorders that benefit from the inhibition of SGLT2.

One aspect of the invention includes a method of preparing the compound of Formula 1 by treating the compound of Formula 28a/b with a hydrogenolysis agent under acidic conditions. Another aspect of the invention includes the method of preparing the compound of Formula 1 as previously presented wherein the hydrogenolysis agent is hydrogen in the presence of palladium. In yet another aspect of the invention, the method of preparing the compound of Formula 1 also includes treating the compound of Formula 28a/b with an acid. Another aspect of the invention further comprises the preparation of Formula 28a/b by reducing a compound of Formula 27 with a reducing agent in the presence of an acid. In another aspect of the invention, the acid is trifluoroacetic acid and the reducing agent is triethylsilane.

Yet another aspect of the invention further comprises the preparation of compound of Formula 27 by treating the compound of Formula 26e with a halogen metal exchange agent and a compound of Formula 22. In a further aspect of the invention, the halogen metal exchange agent is n-butyllithium or hexyllithium.

Yet another aspect the invention further comprises the method of preparing the co-crystal compound of Formula 1 (L-PGA) comprising the compound of Formula 1 and L-pyroglutamic acid in a ratio of approximately 1:1. Another aspect of the invention further includes reslurrying the crystalline compound of Formula 1 (L-PGA) with toluene.

Compounds of the invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements (also available via the *Beilstein* online database)).

For illustrative purposes, the reaction schemes depicted below provide potential routes for synthesizing the compounds of the invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Scheme X1 illustrates the process for preparing the aryl bromide pre-nucleophile compound of Formula 26e from a two step sequence that entails with a halogen metal exchange between 1-bromo-4-ethoxybenzene and an alkyllithium, such n-butyllithium, or with an alkylmagnesium halide, such as i-propylmagnesium chloride, to provide the corresponding Grignard reagent. This newly formed alkyllithium is reacted with 5-bromo-2-chlorobenzaldehyde to afford benzyldryl alcohol 25 which is subsequently treated directly or after isolation with benzyl alcohol in the presence of 0.1 equivalents of sulfuric acid to afford the resulting benzhydryl ether compound of Formula 26e.

Scheme X1

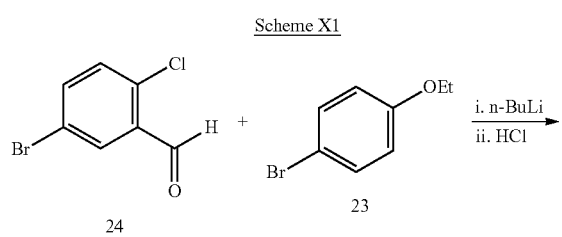

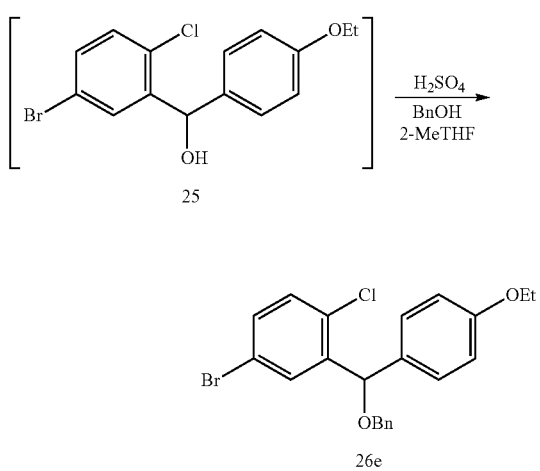

Reaction Scheme X2 illustrates the process for preparing compound of Formula 15 from the tetra-O-benzyl glucose compound of Formula 10.

Scheme X2

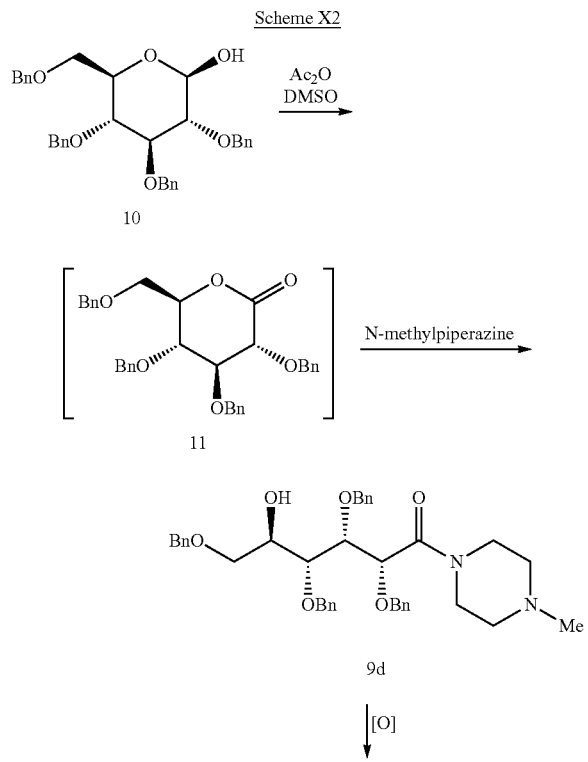

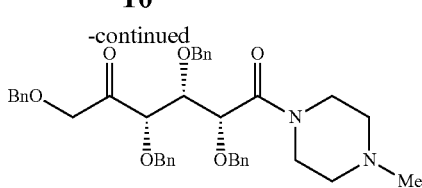

As depicted in Scheme X2, the compound of Formula 15 is prepared by from tetra-OBn-glucose compound of Formula 10 under Albright-Goldman oxidation conditions, acetic anhydride and dimethyl sulfoxide, to afford the lactone compound of Formula 11 in quantitative yield. Other oxidative conditions, such as TPAP-NMO and TEMPO-NaOCl, were shown to also afford the lactone compound of Formula 11 on a preparative scale. Ketoamide compound of Formula 15 is attained by treating lactone compound of Formula 11 with N-methylpiperazine to afford the corresponding amide compound of Formula 9d followed by oxidative conditions.

Scheme X3 illustrates the process for preparing the Grignard reagents represented by Formula 18 and Formula 2, which are essentially hydroxylmethyl synthons.

Scheme X3

A:

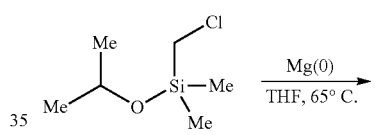

B:

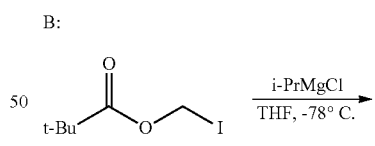

As shown in Scheme X3, Grignard reagents of Formula 18 and Formula 21 are prepared by Approach A and Approach B, respectively. Grignard reagent of Formula 18 is prepared by treating chlormethylsiloxane of Formula 17 with Mg(0) metal in tetrahydrofuran at 65° C. Grignard reagent of Formula 21 is prepared by treating iodomethyl pivalate of Formula 20 with isopropylmethylmagnesium chloride in tetrahydrofuran at −75° C.

Scheme X4 illustrates the process of preparing the diol compound of Formula 19 which involves treating the ketoamide compound of Formula 15 with either Grignard reagent of Formula 18, as represented by condition A or with the Grignard reagent of Formula 21, as represented by condition B.

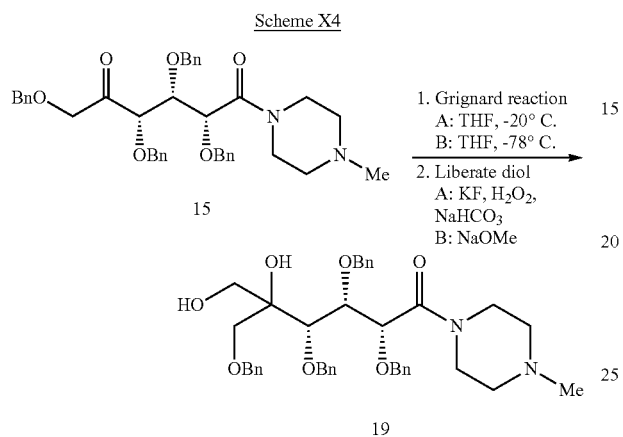

According to Scheme X4 under condition A, ketoamide compound of Formula 15 is treated with the Grignard reagent of Formula 18 in tetrahydrofuran near −20° C. followed by liberating the masked diol compound of Formula 19 under Tamao-Fleming oxidation conditions: potassium chloride, hydrogen peroxide, and sodium bicarbonate. Alternatively, diol compound of Formula 19 is attained by treating ketoamide compound of Formula 15 with Grignard reagent of Formula 21 in tetrahydrofuran at −78° C. followed by treating the mixture with solid sodium methoxide in toluene or cyclopenylmethyl ether to liberate the diol compound of Formula 19. Both Grignard reagents of Formula 18 and Formula 21 exhibited excellent chemoselectivity for addition to the ketone functionality of ketoamide compound of Formula 15. However, the addition of Grignard reagent of Formula 21 to ketoamide compound of Formula 15 exhibited excellent facial selectivity at −78° C. providing a 95:5 mixture of diastereomers at C-5 of compound of Formula 19; whereas, the addition of Grignard reagent of Formula 18 to ketoamide compound of Formula 15 exhibited a more modest facial selectivity at −20° C. providing a 3:2 mixture of diastereomers at C-5 of compound of Formula 19.

Reaction Scheme X5 illustrates the process of preparing the intermediate compound of Formula 22.

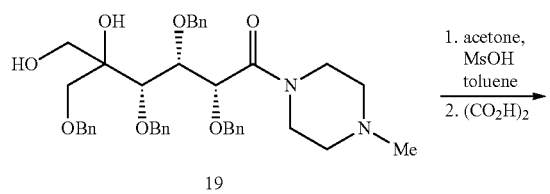

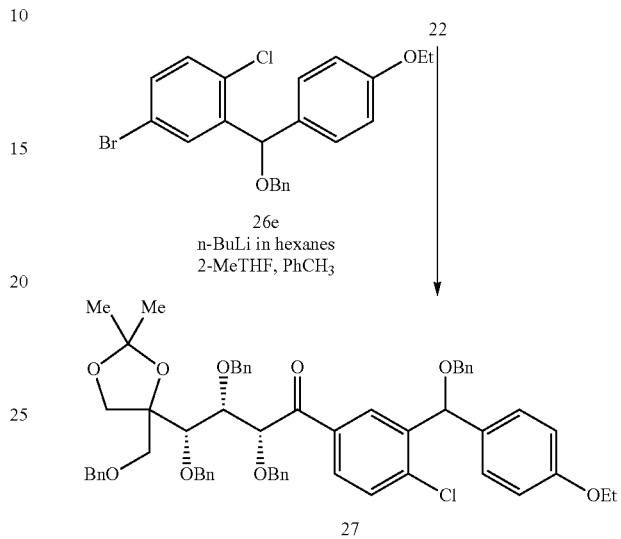

As depicted in Scheme X5, the intermediate compound of Formula 27 is prepared by treating diol compound of Formula 19 with acetone and a catalytic amount of methanesulfonic acid or p-toulenesulfonic acid in toluene as a sticky oil. For purification purposes, the oxalate salt compound of Formula 22 is prepared by treating the intermediate compound of Formula 22 with oxalic acid to afford a stable crystalline salt. The formation of the oxalate salt provided an increased purity level for the intermediate compound 22 which translated to an increased process performance of the subsequent key Grignard reaction. The intermediate compound 22 may be purified to a crystalline free base Formula 22 5R diastereomer by neutralizing the crystalline oxalate salt of Formula 22 with aqueous sodium hydroxide in methyl tert-butyl ether, followed by removal of water via azeotropic distillation with cyclohexane, and isolation of the crystalline free base by filtration. Alternatively, the crystalline oxalate salt of Formula 22 may be neutralized by treatment with solid sodium phosphate or saturated aqueous sodium bicarbonate in toluene at ambient temperature.

Isolated compound of Formula 22 is reacted with the aryllithium nucleophile obtained from treatment of aryl bromide compound of Formula 26e. The corresponding aryllithium nucleophile of the compound of Formula 26e is generated by adding n-butyllithium in hexanes over 10 minutes to the aryl bromide compound of Formula 26e in toluene and 2-methyl tetrahydrofuran at initially −20° C., keeping the internal temperature below −15° C. under positive pressure of nitrogen. Upon completion of the addition of n-butyllithium, the resulting reaction mixture is stirred for 10 to 20 minutes before the addition of free base compound of Formula 22a/b. The free base compound of Formula 22a/b in toluene is added over 10 minutes, while maintaining an internal temperature below −15° C. Upon completion of the reaction as detected by UHPLC analysis, the reaction is quenched with 1N hydrochloric acid and warmed to 20° C.

and subjected to standard work-up conditions to afford the compound of Formula 27 as a crude mixture which is used in the subsequent reaction as outlined in Scheme X6 without further purification.

Reaction Scheme X6 illustrates the process of preparing the compound of Formula 1.

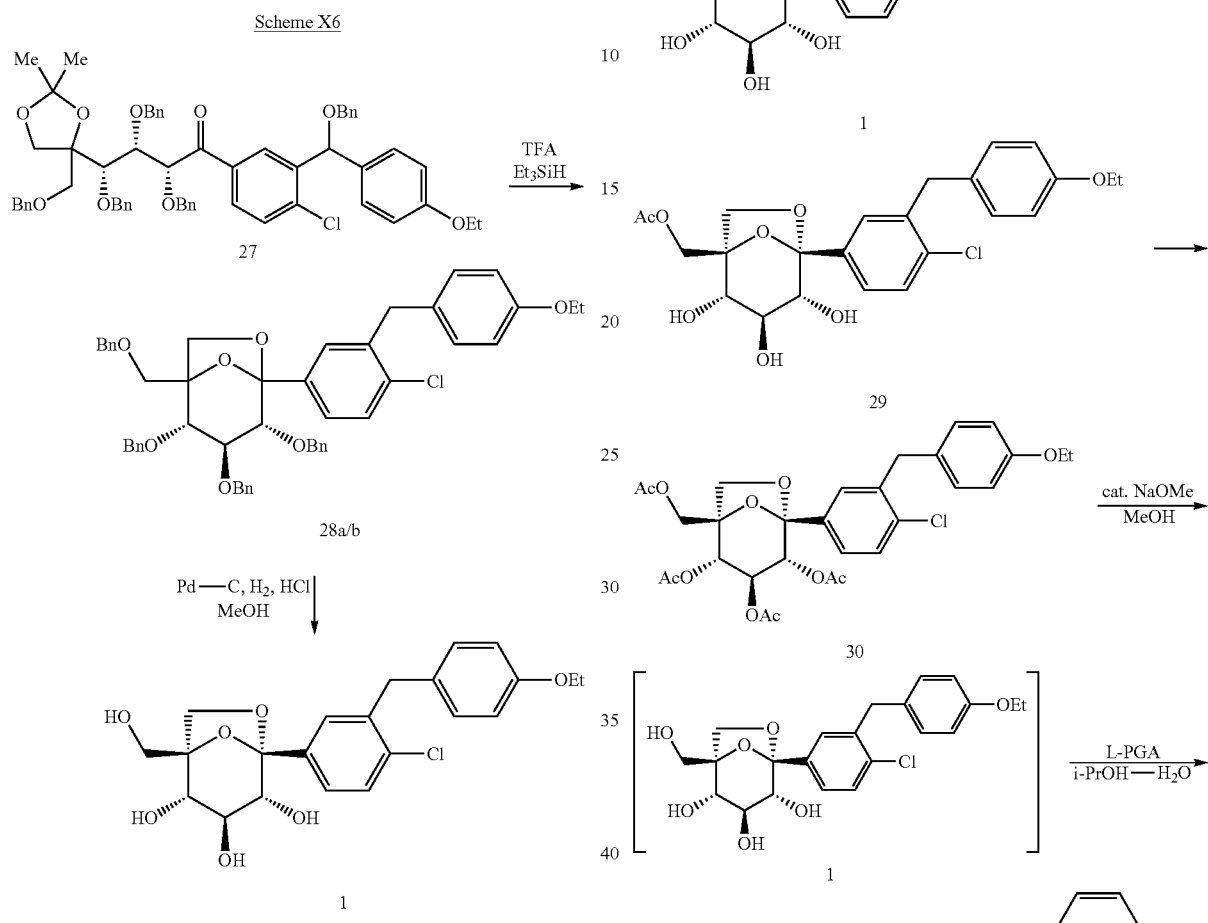

According to Scheme X6, the compound of Formula 1 is prepared by subjecting the unpurified compound of Formula 27 to reductive deprotection condition of trifluoroacetic acid and triethylsilane in toluene at ambient temperature to afford tetrahydropyran intermediate compound of Formula 28a/b as two diastereomers. The crude mixture containing compound of Formula 28a/b can be taken directly into the next step. Intermediate compound of Formula 28a/b is subjected to a pressure reactor for 18 hours under 50 psi at 25° C. charged with 5% Pd/C in methanol:toluene (1:20), 36.5% aqueous hydrochloric acid, and hydrogen to afford the crude mixture containing a single isomeric compound of Formula 1. The crude mixture is typically used directly in the subsequent step as illustrated in Scheme X7. Alternatively, the crude mixture can be purified by silica gel column chromatography to afford an analytically pure SLGT2 inhibitor as a single isomeric compound of Formula 1.

Scheme X7 illustrates the process of preparing cocrystalline compound of Formula 1(L-PGA). Utilization of the crude mixture of compound of Formula 1 directly to the L-PGA cocrystallization procedure provided variable purity. Thus, derivatization of compound of Formula 1 to enable purification via crystallization as needed as outlined in Scheme X7.

As depicted in Scheme X7, monoacetate compound of Formula 29 is formed by treating the crude mixture containing compound of Formula 1 in toluene with pyridine and cooled to −10° C. upon which 1 equivalent of an acylating agent, such as acetic anhydride, is added and subsequently slowly warmed to 20° C. and stirred for 18 hours. For compound of Formula 30, the crude mixture containing compound of Formula 1 in toluene is treated with pyridine, cooled to 5° C., and is treated with an excess of 4 equivalents of acetic anhydride. The resulting mixture is stirred at 5° C. for 1 hour, then at 20° C. for 23 hours to afford tetraacetate compound of Formula 30. Crude compound of Formula 30 is readily recrystallized from a variety of solvents, such as isopropanol, seeded with tetraacetate compound of Formula 30 to yield white crystalline solid.

Following the purity upgrade, tetraacetate compound of Formula 30 is treated with catalytic sodium methoxide in methanol to afford the active deacylated compound of Formula 1 and carried directly to the cocrystallization process without further purification. Unpurified compound of Formula 1 in methanol and isopropanol is treated with L-PGA in water. The resulting mixture is heated to 80° C. and then cooled to 40° C. at 3° C./minute and seeded. The mixture is granulated for 10 hours at 40° C. then further cooled to 20° C. at 0.1° C./minute to afford white crystalline solid of Formula 1 (L-PGA).

Embodiments of the invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

Unless specified otherwise, starting materials are generally available from commercial sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), AstraZeneca Pharmaceuticals (London, England), and Accela ChemBio (San Diego, Calif.).

General Experimental Procedures

NMR spectra were recorded on a Varian Unity™ 400 (available from Varian Inc., Palo Alto, Calif.) at room temperature at 400 MHz for proton. Chemical shifts are expressed in parts per million (delta) relative to residual solvent as an internal reference. The peak shapes are denoted as follows: s, singlet; d, doublet; dd, doublet of doublet; t, triplet; q, quartet; m, multiplet; bs or br.s., broad singlet; 2s, two singlets; br.d., broad doublet. Electrospray ionization mass spectra (ES) were obtained on a Waters™ ZMD instrument (carrier gas: nitrogen; solvent A: water/0.01% formic acid, solvent B: acetonitrile/0.005% formic acid; available from Waters Corp., Milford, Ma.). High resolution mass spectra (HRMS) were obtained on an Agilent™ Model 6210 time of flight. Where the intensity of single chlorine or single bromine-containing ions are described, the expected intensity ratio was observed (approximately 3:1 for $^{35}Cl/^{37}Cl$-containing ions and 1:1 for $^{79}Br/^{81}Br$-containing ions) and the intensity of only the lower mass ion is given. In some cases only representative $^1H$ NMR peaks are given.

Column chromatography was performed with either Baker™ silica gel (40 microm; J. T. Baker, Phillipsburg, N.J.) or Silica Gel 50 (EM Sciences™, Gibbstown, N.J.) in glass columns or in Flash 40 Biotage™ columns (ISC, Inc., Shelton, Conn.). MPLC (medium pressure liquid chromatography) was performed using a Biotage™ SP purification system or a Combiflash® Companion® from Teledyne™ Isco™; Biotage™ SNAP cartridge KPsil or Redisep Rf silica (from Teledyne™ Isco™) under low nitrogen pressure were used. HPLC (high pressure liquid chromatography) was performed using a Shimadzu™ 10A LC-UV or a Agilent™ 1100 preparatory HPLC.

Except where otherwise noted, all reactions were run under an inert atmosphere of nitrogen gas using anhydrous solvents. Also, except where otherwise noted, all reactions were run at room temperature (~23° C.).

When doing TLC (thin layer chromatography), $R_f$ is defined as the ratio of the distance traveled by the compound divided by the distance traveled by the eluent, $R_t$ (retention time).

All reactions were monitored by reverse phase liquid chromatography using a Waters Acquity LC/PDA/SQD equipped with a CSH Phenyl-Hexyl (100×2.1 mm, 1.7 μm) column with a column temperature of 45° C. and a flow rate of 0.4 mL/min. A 30 minute linear gradient with initial conditions of 95% aqueous trifluoroacetic acid and 5% acetonitrile and final conditions of 100% acetonitrile was employed. Approximate retention times (min): compound of Formula 22 (13.3-13.5), compound of Formula 26e (20.1), compound of Formula 27 (25.2-25.6), compound of Formula 28a/b (23.4-23.6), compound of Formula 1 (10.6), compound of Formula 29 (12.6), compound of Formula 30 (17.3).

Figure 2:
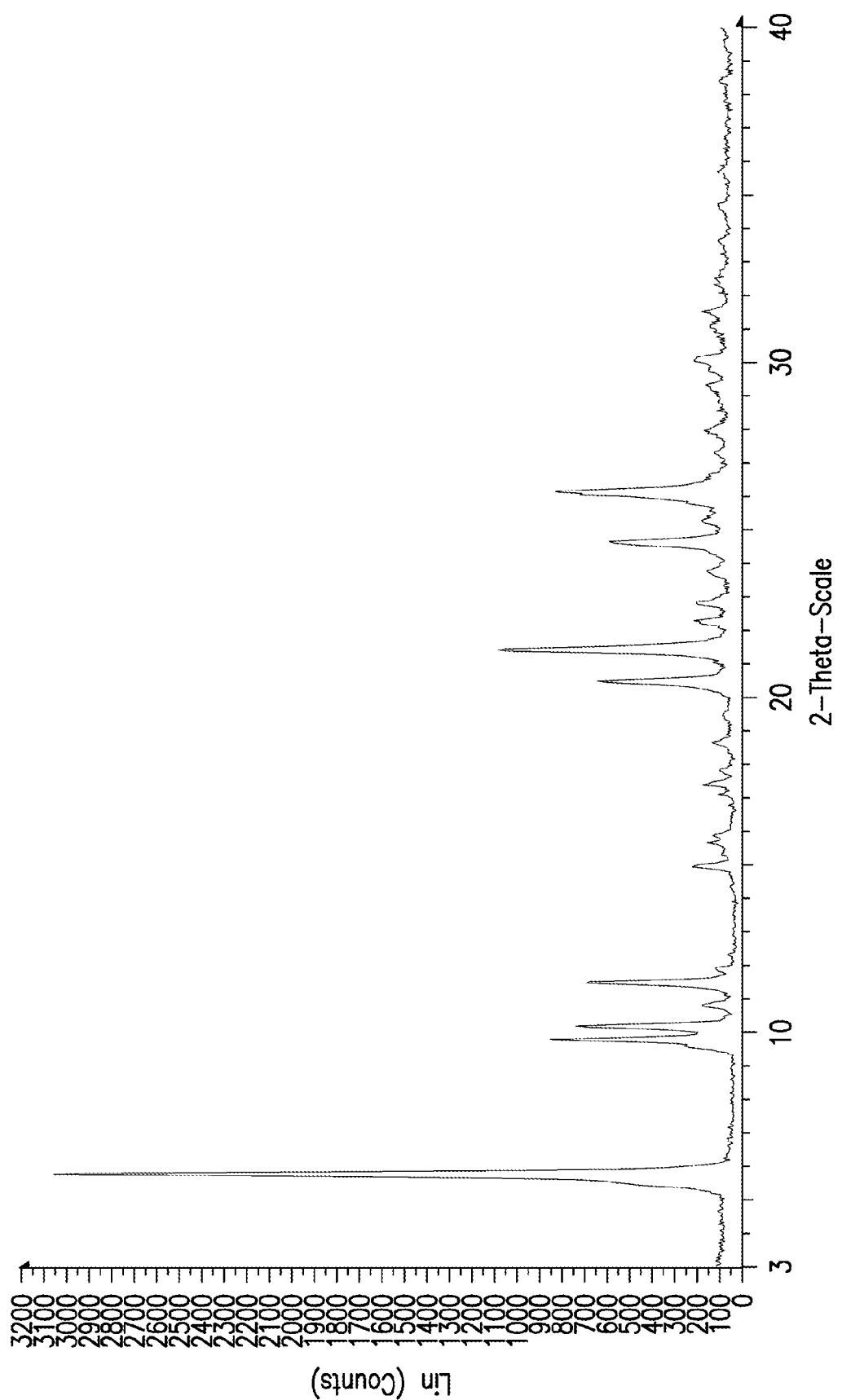
FIG. 2 represents an observed powder X-ray diffraction pattern for the compound of Formula 30.

The powder X-ray diffraction patterns of monoacetate compound of Formula 29 (FIG. 1) and tetraacetate compound of Formula 30 (FIG. 2) were carried out on a Bruker AXS-D8 Advance diffractometer using Cu radiation source. The tube voltage and amperage were set to 40 kV and 40 mA, respectively. The divergence slit was fixed at 1 mm whereas the scattering and the receiving slits were set at 0.6 mm. Diffracted radiation was detected by a scintillation counter detector. Data was collected in the Theta-Theta goniometer at the Cu wavelength $K\alpha_1=1.54056$ Å from 3.0 to 40.0 degrees 2-Theta using a step size of 0.040 degrees and a step time of 2.0 second. Samples were prepared by placement in a Nickel Disk (Gasser & Sons, Inc. Commack, N.Y.) and rotated during data collection. Data were collected and analyzed using Bruker Diffrac Plus software (Version 2.6). Bruker AXS DIFFRACplus Basic EVA 12 software was used to visualize and evaluate the PXRD diffractograms. PXRD data files (.raw) were not processed prior to peak searching. Generally, a Threshold value of 2.0 and a Width value of 0.3 were used to make preliminary peak assignments. The results are summarized in Table 2.

| Table of Definition of Acronyms | |
|---|---|
| Acronym | Definition |
| Ac | Acetyl |
| $Ac_2O$ | Acetic anhydride |
| Bn | Benzyl |
| BnOH | Benzyl alcohol |
| Bu | Butyl |
| CPME | Cyclopentylmethyl ether |
| DMSO | Dimethylsulfoxide |
| DSC | Differential scanning calorimetry |
| Et | Ethyl |
| HPLC | High performance liquid chromatography |
| L-PGA | L-pyroglutamic acid |
| MS | Mass spectrometry |
| MsOH | Methanesulfonic acid |
| Me | Methyl |
| 2-Me THF | 2-methyl tetrahydrofuran |
| NaOMe | Sodium methoxide |
| NMO | N-Methylmorpholine N-oxide |
| Ph | Phenyl |
| $PhCH_3$ | toluene |
| PMB | p-Methoxybenzyl |
| Pr | Propyl |
| SGLT2 | Sodium glucose cotransporter 2 |
| TEMPO | (2,2,6,6-Tetramethylpiperidin-1-yl)oxyl |

-continued

Table of Definition of Acronyms

| Acronym | Definition |
|---|---|
| TFA | Trifluoroacetic acid |
| THF | Tetrahydrofuran |
| TMS | Trimethylsilyl |
| TPAP | Tetrapropylammonium perruthenate |
| p-TsOH | p-Toluenesulfonic acid |
| UHPLC | Ultra high performance liquid chromatography |

Example 1

(2R,3S,4S)-2,3,4-tris(benzyloxy)-1-(3-((benzyloxy) (4-ethoxyphenyl)methyl)-4-chlorophenyl)-4-(4-((benzyloxy)methyl)-2,2-dimethyl-1,3-dioxolan-4-yl)butan-1-one (27)

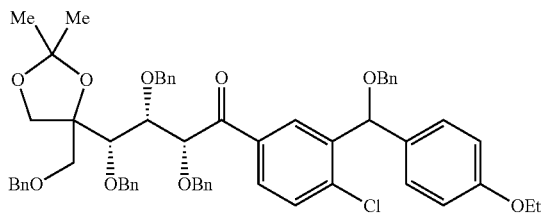

Salt break: (2R,3S,4S)-2,3,4-tris(benzyloxy)-4-(4-((benzyloxy)methyl)-2,2-dimethyl-1,3-dioxolan-4-yl)-1-(4-methylpiperazin-1-yl)butan-1-one oxalate (22) (10.09 g, 12.63 mmol) and toluene (100 mL) were combined in a suitable reaction vessel to afford a white suspension at ambient temperature. A solution of saturated aqueous sodium bicarbonate (55 mL) was then added slowly to the oxalate salt slurry, and the resulting mixture was allowed to stir for 10 minutes. The reaction mixture was transferred into a separatory funnel and the aqueous phase (pH 7) was removed. The organic phase was washed with additional saturated aqueous sodium bicarbonate (20 mL, pH 9) then was dried over sodium sulfate, filtered and concentrated to an orange brown solution (ca. 15 mL).

Lithiation: (2-((benzyloxy)(4-ethoxyphenyl)methyl)-4-bromo-1-chlorobenzene (26e) (6.49 g, 15.03 mmol), toluene (60 mL) and 2-methyl tetrahydrofuran (6.5 mL) were charged to a second reaction vessel to afford a clear, colorless solution. This was cooled to −20° C. with stirring under a positive pressure of nitrogen. A solution of n-butyllithium in hexane (2.5 mol/L, 6.5 mL) was then added over 10 minutes, while keeping the internal temperature below −15° C. Following complete addition, the reaction was allowed to stir for 10-20 minutes before use in the arylation step.

Arylation: The solution of free base (2R,3S,4S)-2,3,4-tris(benzyloxy)-4-(4-((benzyloxy)methyl)-2,2-dimethyl-1,3-dioxolan-4-yl)-1-(4-methylpiperazin-1-yl)butan-1-one (22) in toluene was then added over 10 minutes, while keeping the internal temperature below −15° C. After complete addition, UHPLC analysis confirmed reaction completion. The reaction was therefore quenched via addition of 1N hydrochloric acid (50 mL), and was then warmed to 20° C. The phases were separated and the organic phase was washed with saturated aqueous sodium chloride (30 mL), dried with sodium sulfate, filtered and concentrated to an orange-brown oil. The crude product oil was purified by silica gel column chromatography using an ethyl acetate/hexanes gradient as eluent to afford a mixture of stereoisomers of (2R,3S,4S)-2,3,4-tris(benzyloxy)-1-(3-((benzyloxy) (4-ethoxyphenyl) methyl)-4-chlorophenyl)-4-(4-((benzyloxy)methyl)-2,2-dimethyl-1,3-dioxolan-4-yl)butan-1-one (27) (10.83 g, 11.26 mmol, 89% yield). Alternately, the crude, partially concentrated solution of (2R,3S,4S)-2,3,4-tris(benzyloxy)-1-(3-((benzyloxy)(4-ethoxyphenyl)methyl)-4-chlorophenyl)-4-(4-((benzyloxy)methyl)-2,2-dimethyl-1,3-dioxolan-4-yl) butan-1-one (27) may be used directly without chromatography.

$^1$H NMR (DMSO-$d_6$, 600 MHz, 25° C.): δ 8.47 (d, J=2.0 Hz, 1H), 8.41 (d, J=2.0 Hz, 1H), 7.89 (dd, J=8.3, 2.0 Hz, 1H), 7.88 (dd, J=8.3, 2.0 Hz, 1H), 7.47 (d, J=8.3 Hz, 1H), 7.46 (d, J=8.3 Hz, 1H), 7.31-7.15 (m, 25H), 7.03 (d, J=7.6 Hz, 2H), 7.01 (d, J=7.6 Hz, 2H), 6.80 (d, J=8.6 Hz, 2H), 6.79 (d, J=8.6 Hz, 2H), 5.77 (s, 1H), 5.76 (s, 1H), 5.00 (m, 2H), 4.69 (d, J=11.7 Hz, 1H), 4.68 (d, J=11.7 Hz, 1H), 4.64-4.53 (m, 4H), 4.49-4.30 (m, 14H), 3.94-3.89 (m, 4H), 3.88-3.85 (m, 4H), 3.71 (d, J=11.2 Hz, 1H), 3.69 (d, J=11.2 Hz, 1H), 3.51-3.43 (m, 4H), 1.29 (s, 3H), 1.28 (s, 3H), 1.26 (t, J=7.0 Hz, 3H), 1.25 (t, J=7.0 Hz, 3H), 1.11 (s, 3H), 1.10 (s, 3H).

$^{13}$C NMR (DMSO-$d_6$, 150 MHz, 25° C.): δ 198.18, 197.96, 158.05, 139.91, 139.88, 138.33, 138.30, 137.83, 137.80, 137.76, 137.65, 137.58, 137.46, 137.41, 136.89, 136.76, 134.86, 134.74, 131.23, 131.18, 129.74, 129.69, 128.95, 128.89, 128.83, 128.62, 128.18, 128.16, 128.14, 128.01, 127.95, 127.79, 127.65, 127.60, 127.56, 127.50, 127.47, 127.46, 127.41, 127.28, 127.26, 127.20, 127.17, 127.11, 127.09, 127.06, 114.11, 108.84, 108.74, 84.73, 84.66, 84.37, 84.18, 78.94, 78.76, 78.36, 78.33, 78.10, 77.81, 74.17, 74.02, 73.78, 73.74, 72.58, 72.50, 72.11, 72.03, 71.58, 71.49, 70.01, 69.96, 68.09, 67.94, 62.85, 48.64, 27.10, 27.05, 26.74, 26.03, 14.49, 14.48.

HRMS: (ESI$^+$) Calcd for $C_{60}H_{61}Cl_1O_9Na$ (M+Na)$^+$: 983.38963, Found: 983.39026.

Example 2

(2S,3S,4R)-2,3,4-tris(benzyloxy)-1-((benzyloxy) methyl)-5-(4-chloro-3-(4-ethoxybenzyl)phenyl)-6,8-dioxabicyclo[3.2.1]octane (28a/b) and (1R,2S,3S, 4R,5R)-2,3,4-tris(benzyloxy)-1-((benzyloxy) methyl)-5-(4-chloro-3-(4-ethoxybenzyl)phenyl)-6,8-dioxabicyclo[3.2.1]octane (28a)

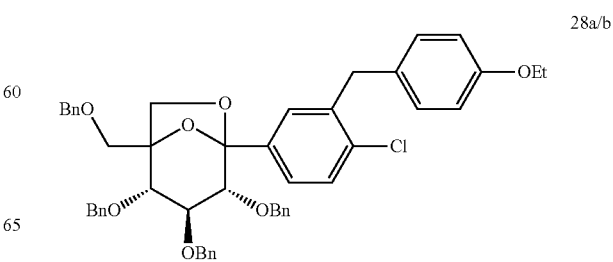

-continued

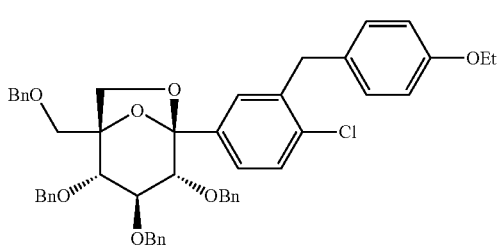

28a

A solution of (2R,3S,4S)-2,3,4-tris(benzyloxy)-1-(3-((benzyloxy)(4-ethoxyphenyl)methyl)-4-chlorophenyl)-4-(4-((benzyloxy)methyl)-2,2-dimethyl-1,3-dioxolan-4-yl)butan-1-one (27) (8.06 g, 8.38 mmol) and toluene (40 mL) was treated with trifluoroacetic acid (3.2 mL) and triethylsilane (10.4 mL, 7.57 g, 65.11 mmol) at ambient temperature in a suitable reaction vessel. After complete reaction, according to UHPLC-MS analysis, saturated aqueous sodium bicarbonate was added. The layers were separated, the organic phase was washed with water and saturated aqueous sodium chloride, and then dried over sodium sulfate, filtered and concentrated to an oil. The crude oil was purified by silica gel column chromatography using an ethyl acetate:hexanes gradient as eluent to afford the major stereoisomer, 28a (5.56 g). Alternately, the crude, partially concentrated solution of (2S,3S,4R)-2,3,4-tris(benzyloxy)-1-((benzyloxy)methyl)-5-(4-chloro-3-(4-ethoxybenzyl)phenyl)-6,8-dioxabicyclo[3.2.1]octane (28a/b) may be used directly without chromatography. Data for major stereoisomer, 28a:

$^1$H NMR (28a, DMSO-$d_6$, 500 MHz, 25° C.): δ 7.43 (d, J=2.5 Hz, 1H), 7.71-7.14 (m, 21H), 7.03 (d, J=8.6 Hz, 2H), 6.86 (d, J=7.3 Hz, 2H), 6.73 (d, J=8.6 Hz, 2H), 4.57 (s, 2H), 4.56 (d, J=12.2 Hz, 1H), 4.52 (d, J=11.4 Hz, 1H), 4.48 (d, J=12.2 Hz, 1H), 4.41 (d, J=11.4 Hz, 1H), 4.21 (d, J=11.8 Hz, 1H), 4.14 (d, J=7.0 Hz, 1H), 4.02 (d, J=11.8 Hz, 1H), 3.98 (s, 2H), 3.96 (d, J=9.4 Hz, 1H), 3.91 (q, J=7.0 Hz, 2H), 3.86 (s, 1H), 3.71 (d, J=7.0 Hz, 1H), 3.64 (d, J=9.4 Hz, 1H), 3.61 (s, 1H), 3.57 (s, 1H), 1.27 (t, J=7.0 Hz, 3H).

$^{13}$C NMR (28a, DMSO-$d_6$, 125 MHz, 25° C.): δ 156.8, 138.1, 138.0, 137.92, 137.88, 137.61, 132.8, 131.1, 129.4, 128.8, 128.6, 128.33, 128.28, 128.15, 128.1, 127.9, 127.8, 127.68, 127.66, 127.63, 127.58, 127.51, 127.4, 125.6, 114.2, 106.5, 82.7, 76.8, 75.1, 74.5, 72.9, 71.3, 71.1, 70.9, 68.9, 68.3, 62.8, 37.5, 14.6.

HRMS (28a): (ESI$^+$) Calcd for $C_{50}H_{49}Cl_1O_7Na$ (M+Na)$^+$: 819.30590, Found: 819.30676.

Example 3

(1S,2S,3S,4R,5S)-5-(4-chloro-3-(4-ethoxybenzyl)phenyl)-1-(hydroxymethyl)-6,8-dioxabicyclo[3.2.1]octane-2,3,4-triol (1)

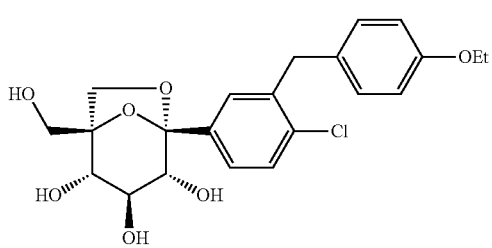

1

A pressure reactor was charged with 5% Pd/C (Johnson Matthey type A5R87L, 20 wt %, 2.8 g). A solution of tetra-O-benzyl ether isomers (2S,3S,4R)-2,3,4-tris(benzyloxy)-1-((benzyloxy)methyl)-5-(4-chloro-3-(4-ethoxybenzyl)phenyl)-6,8-dioxabicyclo[3.2.1]octane (28a/b)(14 g, 17.55 mmol) in methanol (2 mL/g, 28 mL) and toluene (40 mL/g, 560 mL) was then added, followed by 36.5% aqueous hydrochloric acid (2.39 mL). The vessel was purged successively with nitrogen (4×) and hydrogen (4×), and then the slurry was warmed to 25° C. The vessel was then pressurized to 50 psi with hydrogen and stirred for 18 hours. The vessel was then purged with nitrogen (4×). The catalyst was removed via filtration and the cake was washed with methanol. UHPLC analysis indicated complete conversion to (1S,2S,3S,4R,5S)-5-(4-chloro-3-(4-ethoxybenzyl)phenyl)-1-(hydroxymethyl)-6,8-dioxabicyclo[3.2.1]octane-2,3,4-triol (1). The crude product was typically utilized directly in the subsequent step; however, a portion of the mixture was purified by silica gel column chromatography to afford an analytically pure sample of (1S,2S,3S,4R,5S)-5-(4-chloro-3-(4-ethoxybenzyl)phenyl)-1-(hydroxymethyl)-6,8-dioxabicyclo[3.2.1]octane-2,3,4-triol (1) as a white solid after concentration.

$^1$H NMR (DMSO-$d_6$, 600 MHz, 25° C.): δ 7.40 (d, J=2.1 Hz, 1H), 7.39 (d, J=8.3 Hz, 1H), 7.30 (dd, J=8.3, 2.1 Hz, 1H), 7.09 (d, J=8.6 Hz, 2H), 6.83 (d, J=8.6 Hz, 2H), 5.19 (d, J=5.5, 1H), 4.97 (d, J=5.6, 1H), 4.89 (d, J=6.7, 1H), 4.75 (t, J=6.0, 1H), 3.99 (s, 2H), 3.98 (d, J=7.0 Hz, 1H), 3.97 (q, J=6.9 Hz, 1H), 3.63 (dd, J=12.4, 6.0 Hz, 1H), 3.54 (dd, J=7.9, 5.5 Hz, 1H), 3.49 (dd, J=12.4, 6.0 Hz, 1H), 3.46 (d, J=7.0 Hz, 1H), 3.43 (td, J=7.9, 5.6 Hz, 1H), 3.40 (dd, J=7.8, 6.8 Hz, 1H), 1.30 (t, J=6.9 Hz, 3H).

$^{13}$C NMR (DMSO-$d_6$, 150 MHz, 25° C.): δ 156.8, 138.0, 137.6, 132.5, 131.0, 129.5, 129.2, 128.3, 126.1, 114.2, 107.6, 84.9, 77.3, 76.0, 71.4, 66.1, 62.8, 59.8, 37.5, 14.6.

HRMS: (ESI$^-$) Calcd for $C_{22}H_{24}Cl_1O_7$ (M–H)$^-$: 435.12160, Found: 435.11993.

Example 4

(1R,2S,3S,4R,5S)-5-(4-chloro-3-(4-ethoxybenzyl)phenyl)-2,3,4-trihydroxy-6,8-dioxabicyclo[3.2.1]octan-1-yl)methyl acetate (29)

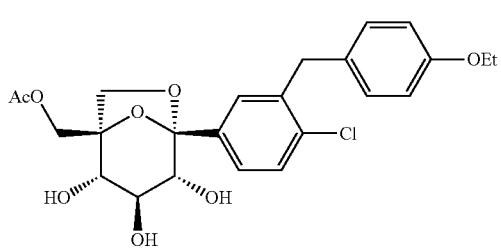

29

A solution of (1S,2S,3S,4R,5S)-5-(4-chloro-3-(4-ethoxybenzyl)phenyl)-1-(hydroxymethyl)-6,8-dioxabicyclo[3.2.1]octane-2,3,4-triol (1) (26.4 g, 60.43 mmol) in toluene (270 mL) and pyridine (6.6 mL) was charged to a suitable reaction vessel. The solution was cooled to –10° C., and then acetic anhydride (5.8 mL, 1 equivalent) was added over 5 minutes. The reaction was stirred for 60 minutes at –10° C., and then was warmed slowly to 20° C. and stirred for 18 hours to provide a slurry. Toluene (100 mL) was then added, followed by water (200 mL). After stirring for 15 minutes, the water layer was removed and the solids were collected by filtration. The cake was washed with additional water and toluene, then solids were dried under vacuum at room temperature to provide ((1R,2S,3S,4R,5S)-5-(4-chloro-3-(4-ethoxybenzyl)phenyl)-2,3,4-trihydroxy-6,8-dioxabicyclo[3.2.1]octan-1-yl)methyl acetate (29) as a white solid (19.2 g). UHPLC/MS: 97.6% product, 2.0% C-4 acetate isomer, 0.4% (1S,2S,3S,4R,5S)-5-(4-chloro-3-(4-ethoxybenzyl)phenyl)-1-(hydroxymethyl)-6,8-dioxabicyclo[3.2.1]octane-2,3,4-triol.

$^1$H NMR (DMSO-$d_6$, 500 MHz, 25° C.): δ 7.400 (d, J=8.3 Hz, 1H), 7.398 (d, J=2.1 Hz, 1H), 7.30 (dd, J=8.3, 2.1 Hz, 1H), 7.09 (d, J=8.7 Hz, 2H), 6.83 (d, J=8.7 Hz, 2H), 5.50 (d, J=5.7 Hz, 1H), 5.10 (d, J=5.6 Hz, 1H), 5.01 (d, J=6.6 Hz, 1H), 4.27 (d, J=12.4 Hz, 1H), 4.07 (d, J=12.4 Hz, 1H), 4.06 (d, J=7.4 Hz, 1H), 3.99 (s, 2H), 3.97 (q, J=7.0 Hz, 2H), 3.58 (t, J=6.5 Hz, 1H), 3.50 (dd, J=7.4, 0.9 Hz, 1H), 3.44 (m, 1H), 3.42 (m, 1H), 2.02 (s, 3H), 1.29 (t, J=7 Hz, 3H).

$^{13}$C NMR (DMSO-$d_6$, 125 MHz, 25° C.): δ 170.1, 156.9, 137.8, 137.6, 132.7, 131.1, 129.6, 129.2, 128.5, 126.1, 114.3, 108.2, 82.8, 77.2, 75.7, 71.2, 66.4, 62.8, 62.0, 37.6, 20.6, 14.7.

HRMS: (ESI$^+$) Calcd for $C_{24}H_{28}ClO_8$ (M+H)$^+$: 479.14672, Found: 479.14630.

TABLE 2

List of Powder X-ray diffraction peaks of
Compound of Formula 29
Compound of Formula 29
peak selection intensity ≥20%

| Angle (°2-Theta) | Intensity* (relative) % |
|---|---|
| 5.8 | 100 |
| 6.4 | 22.3 |
| 11.6 | 20.1 |
| 13.7 | 20.3 |
| 14.4 | 21.3 |
| 15.0 | 25.5 |
| 16.0 | 74.1 |
| 16.6 | 42.8 |
| 17.4 | 46.9 |
| 19.3 | 26.8 |
| 19.9 | 32.1 |
| 21.0 | 20.7 |
| 21.6 | 73.7 |
| 23.7 | 34.7 |

*The peak intensities may change depending on the crystal size and habit

Example 5

(1R,2S,3S,4R,5S)-1-(acetoxymethyl)-5-(4-chloro-3-(4-ethoxybenzyl)phenyl)-6,8-dioxabicyclo[3.2.1]octane-2,3,4-triyl triacetate (30)

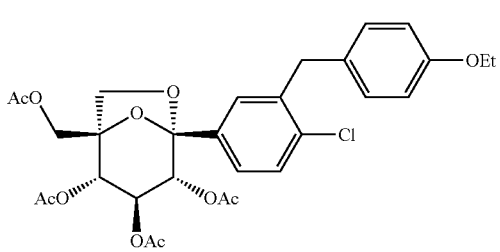

A solution of (1S,2S,3S,4R,5S)-5-(4-chloro-3-(4-ethoxybenzyl)phenyl)-1-(hydroxymethyl)-6,8-dioxabicyclo[3.2.1]octane-2,3,4-triol (1) (83 g, 189.98 mmol), toluene (830 mL) and pyridine (122 mL) was cooled to 5° C. with stirring. Acetic anhydride (108 mL, 6 equivalents) was then added over 15 minutes. Following complete addition, the reaction was stirred at 5° C. for 1 hour then at 20° C. for 23 hours. The reaction mixture was then cooled to 5° C. where water (800 mL) was added over 10 minutes. The resulting mixture was stirred at 5° C. for 15 minutes then was warmed to 20° C. before the phases were separated. The organic phase was then washed with water (500 mL), dried over magnesium sulfate, filtered and concentrated at 40° C./50 torr to an oil. Isopropanol (1.2 L) was added and the resulting solid-liquid mixture was heated to 60° C. to provide a solution. This solution was cooled to 45° C. over 1 hour and then seeded with (1R,2S,3S,4R,5S)-1-(acetoxymethyl)-5-(4-chloro-3-(4-ethoxybenzyl)phenyl)-6,8-dioxabicyclo[3.2.1]octane-2,3,4-triyl triacetate (30) (50 mg). This resulted in formation of a thick slurry that was thinned by the addition of isopropanol (100 mL). The solids were collected after 1 hour at 20° C.; the cake was washed with isopropanol (2×100 mL) and dried under vacuum to afford (1R,2S,3S,4R,5S)-1-(acetoxymethyl)-5-(4-chloro-3-(4-ethoxybenzyl)phenyl)-6,8-dioxabicyclo[3.2.1]octane-2,3,4-triyl triacetate (30) as a white crystalline solid (102.0 g, 168.59 mmol, 89% yield). UHPLC/MS purity: 99.6%, 0.4% triacetate. The crystallization liquors were concentrated to 300 mL at 40° C./40 torr. The resulting slurry was stirred at 20° C. for 1 hour, and then solids were collected, washed with isopropanol and dried under vacuum at 20° C. This provided a second crop of (1R,2S,3S,4R,5S)-1-(acetoxymethyl)-5-(4-chloro-3-(4-ethoxybenzyl)phenyl)-6,8-dioxabicyclo[3.2.1]octane-2,3,4-triyltriacetate (30) (6.2 g) of slightly lower purity (UHPLC/MS purity: 93.7%, 6.3% triacetate).

$^1$H NMR (DMSO-$d_6$, 500 MHz, 25° C.): δ 7.46 (d, J=8.3 Hz, 1H), 7.39 (d, J=2.1 Hz, 1H), 7.33 (dd, J=8.3, 2.1 Hz, 1H), 7.06 (d, J=8.6 Hz, 2H), 6.83 (d, J=8.7 Hz, 2H), 5.35 (dd, J=8.4, 0.8 Hz, 1H), 5.25 (t, J=8.4 Hz, 1H), 5.19 (d, J=8.4 Hz, 1H), 4.47 (d, J=12.8 Hz, 1H), 4.34 (d, J=8.4 Hz, 1H), 4.04 (d, J=12.8 Hz, 1H), 4.03 (d, J=15.2 Hz, 1H), 3.97 (d, J=15.2 Hz, 1H), 3.97 (q, J=7.0 Hz, 2H), 3.79 (dd, J=8.4, 0.8 Hz, 1H), 2.02 (s, 3H), 2.00 (s, 3H), 1.92 (s, 3H), 1.66 (s, 3H), 1.29 (t, J=7 Hz, 3H).

$^{13}$C NMR (DMSO-$d_6$, 125 MHz, 25° C.): δ 169.71, 169.70, 169.1, 168.6, 157.0, 138.6, 134.4, 133.9, 130.9, 129.5, 129.2, 128.7, 125.4, 114.3, 106.9, 82.6, 74.8, 72.2, 68.7, 67.9, 62.9, 60.4, 37.4, 20.39, 20.36, 20.32, 19.9, 14.6.

HRMS: (ESI$^+$) Calcd for $C_{30}H_{33}ClO_{11}Na$ (M+Na)$^+$: 627.16036, Found: 627.16211.

TABLE 3

List of Powder X-ray diffraction peaks of
Compound of Formula 30
Compound of Formula 30
peak selection intensity ≥5%

| Angle (°2-Theta) | Intensity* (relative) % |
|---|---|
| 5.7 | 100 |
| 9.7 | 27.7 |
| 10.1 | 24 |
| 10.8 | 5.6 |
| 11.5 | 22.4 |
| 14.9 | 7 |
| 17.4 | 5.5 |
| 20.5 | 20.8 |
| 21.4 | 35.3 |
| 22.3 | 6.8 |
| 22.8 | 6.5 |

TABLE 3-continued

List of Powder X-ray diffraction peaks of
Compound of Formula 30
Compound of Formula 30
peak selection intensity ≥5%

| Angle (°2-Theta) | Intensity* (relative) % |
|---|---|
| 24.6 | 19.1 |
| 25.2 | 5.7 |
| 26.1 | 27 |
| 28.0 | 5.3 |
| 29.3 | 5.1 |
| 30.1 | 6.8 |
| 31.5 | 5.6 |

*The peak intensities may change depending on the crystal size and habit

Example 6

(1S,2S,3S,4R,5S)-5-(4-chloro-3-(4-ethoxybenzyl) phenyl)-1-(hydroxymethyl)-6,8-dioxabicyclo[3.2.1] octane-2,3,4-triol, (1:1) compound with (S)-5-oxopyrrolidine-2-carboxylic acid (1 (L-PGA))

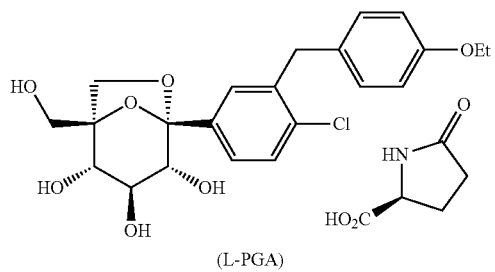

(L-PGA)

Deacetylation: To a stirring solution of NaOMe (0.5M in MeOH, 0.65 mL) in MeOH (40 mL) at 20° C. was added (1R,2S,3S,4R,5S)-1-(acetoxymethyl)-5-(4-chloro-3-(4-ethoxybenzyl)phenyl)-6,8-dioxabicyclo[3.2.1]octane-2,3,4-triyl triacetate (30) (20.0 g, 33.06 mmol) in two solid portions separated by 15 minutes. The additions provided a slurry that gave way to a solution after a few minutes. After stirring for ca. 3 hours, UHPLC-MS analysis of an aliquot indicated <2% combined ((1R,2S,3S,4R,5S)-5-(4-chloro-3-(4-ethoxybenzyl)phenyl)-2,3,4-trihydroxy-6,8-dioxabicyclo [3.2.1]octan-1-yl)methyl acetate intermediate, so the crude solution was carried directly into the subsequent cocrystallization step. For the purpose of characterization, a small portion of the mixture was concentrated to dryness on a rotovap, and then further dried under high vacuum, to provide amorphous (1S,2S,3S,4R,5S)-5-(4-chloro-3-(4-ethoxybenzyl)phenyl)-1-(hydroxymethyl)-6,8-dioxabicyclo [3.2.1]octane-2,3,4-triol (1) as a white solid mass.

$^1$H NMR (DMSO-d$_6$, 600 MHz, 25° C.): δ 7.40 (d, J=2.1 Hz, 1H), 7.39 (d, J=8.3 Hz, 1H), 7.30 (dd, J=8.3, 2.1 Hz, 1H), 7.09 (d, J=8.6 Hz, 2H), 6.83 (d, J=8.6 Hz, 2H), 5.19 (d, J=5.5, 1H), 4.97 (d, J=5.6, 1H), 4.89 (d, J=6.7, 1H), 4.75 (t, J=6.0, 1H), 3.99 (s, 2H), 3.98 (d, J=7.0 Hz, 1H), 3.97 (q, J=6.9 Hz, 2H), 3.63 (dd, J=12.4, 6.0 Hz, 1H), 3.54 (dd, J=7.9, 5.5 Hz, 1H), 3.49 (dd, J=12.4, 6.0 Hz, 1H), 3.46 (d, J=7.0 Hz, 1H), 3.43 (td, J=7.9, 5.6 Hz, 1H), 3.40 (dd, J=7.8, 6.8 Hz, 1H), 1.30 (t, J=6.9, 3H).

$^{13}$C NMR (DMSO-d$_6$, 150 MHz, 25° C.): δ 156.8, 138.0, 137.6, 132.5, 131.0, 129.5, 129.2, 128.3, 126.1, 114.2, 107.6, 84.9, 77.3, 76.0, 71.4, 66.1, 62.8, 59.8, 37.5, 14.6.

HRMS: (ESI$^-$) Calcd for C$_{22}$H$_{24}$Cl$_1$O$_7$ (M–H)$^-$: 435.12160, Found: 435.11993.

Cocrystal formation: A solution of (1S,2S,3S,4R,5S)-5-(4-chloro-3-(4-ethoxybenzyl)phenyl)-1-(hydroxymethyl)-6,8-dioxabicyclo[3.2.1]octane-2,3,4-triol (1) (4.80 g, 10.99 mmol) in MeOH (17.3 mL) was concentrated under vacuum (30 Torr) at 40° C. to minimal volume. The residue was taken up in i-PrOH (18.7 mL) and the resulting solution was passed through a speck free filter into a suitable reaction vessel. The solution was heated to 60° C. where water (18.7 mL) was added. In a second reaction vessel, L-pyroglutamic acid (3.91 g, 30.28 mmol) was dissolved in water (56.2 mL). This solution was passed through a speck free filter into the reactor containing (1S,2S,3S,4R,5S)-5-(4-chloro-3-(4-ethoxybenzyl)phenyl)-1-(hydroxymethyl)-6,8-dioxabicyclo [3.2.1]octane-2,3,4-triol (1). The resulting mixture was heated to 80° C., and then was cooled to 40° C. at 3° C./minute and seeded. The mixture was granulated for 10 hours at 40° C., and then cooled to 20° C. at 0.1° C./min. The resulting white slurry was isolated on a Coors filter, washed with toluene (2×9.8 mL), and was dried under vacuum at 55° C. for 4 hours to provide (1S,2S,3S,4R,5S)-5-(4-chloro-3-(4-ethoxybenzyl)phenyl)-1-(hydroxymethyl)-6,8-dioxabicyclo[3.2.1]octane-2,3,4-triol cocrystal with (S)-5-oxopyrrolidine-2-carboxylic acid as a white crystalline solid (1 (L-PGA)) (5.26 g, 9.29 mmol, 85% yield).

$^1$H NMR (DMSO-d$_6$, 600 MHz, 25° C.): δ 7.90 (bs, 1H), 7.40 (d, J=2.1 Hz, 1H), 7.39 (d, J=8.3 Hz, 1H), 7.30 (dd, J=8.3, 2.1 Hz, 1H), 7.09 (d, J=8.6 Hz, 2H), 6.83 (d, J=8.6 Hz, 2H), 5.19 (bs, 1H), 4.97 (bs, 1H), 4.90 (bs, 1H), 4.75 (bs, 1H), 4.06 (ddd, J=9.0, 4.3, 0.7 Hz, 1H), 3.99 (s, 2H), 3.98 (d, J=7.2 Hz, 1H), 3.97 (q, J=7.0 Hz, 2H), 3.63 (dd, J=12.5, 4.5 Hz, 1H), 3.54 (d, J=7.8 Hz, 1H), 3.49 (dd, J=12.5, 4.5 Hz, 1H), 3.46 (d, J=7.2 Hz, 1H), 3.43 (t, J=7.9 Hz, 1H), 3.40 (dd, J=7.9, 5.5 Hz, 1H), 2.32 (m, 1H), 2.12 (m, 2H), 1.96 (m, 1H), 1.30 (t, J=7.0, 3H).

$^{13}$C NMR (DMSO-d$_6$, 150 MHz, 25° C.): δ 176.9, 174.3, 156.8, 138.0, 137.6, 132.5, 131.0, 129.5, 129.2, 128.3, 126.1, 114.2, 107.6, 84.9, 77.3, 76.0, 71.4, 66.1, 62.8, 59.8, 54.6, 37.5, 28.9, 24.5, 14.6.

HRMS: (ESI$^-$) Calcd for C$_{27}$H$_{31}$Cl$_1$N$_1$O$_{10}$ (M–H)$^-$: 564.16420, Found: 564.16315.

Single crystals were obtained by slow solvent evaporation method using ethyl acetate as the solvent. The API was dissolved in ethyl acetate by heating the solution to about 50-60° C. until a clear solution was obtained. The solution was kept at room temperature for slow solvent evaporation. *Single Crystal X-Ray Analysis.* A representative crystal was surveyed and a 1 Å data set (maximum sin Θ/λ=0.5) was collected on a Bruker APEX diffractometer. Friedel pairs were collected in order to facilitate the determination of the absolute configuration. Atomic scattering factors were taken from the International Tables for Crystallography. See, *International Tables for Crystallography*, Vol. C, pp. 219, 500, Kluwer Academic Publishers, 1992. All crystallographic calculations were facilitated by the SHELXTL system. See, *SHELXTL*, Version 5.1, Bruker AXS, (1997). All diffraction data were collected at room temperature. Pertinent crystal, data collection, and refinement are summarized in Table 1 below.

TABLE 1

Crystal data and structure refinement for Example 6.

| | |
|---|---|
| Empirical formula | C$_{27}$H$_{32}$ClNO$_{10}$ |
| Formula weight | 565.99 |
| Temperature | 298(2) K |
| Wavelength | 1.54178 Å |
| Crystal system | Orthorhombic |
| Space group | P2(1)2(1)2(1) |
| Unit cell dimensions | a = 7.4559(2) Å    α = 90°. |
| | b = 12.8477(4) Å  β = 90°. |
| | c = 27.9870(8) Å  γ = 90°. |

TABLE 1-continued

Crystal data and structure refinement for Example 6.

| | |
|---|---|
| Volume | 2680.91(13) Å$^3$ |
| Z | 4 |
| Density (calculated) | 1.402 Mg/m$^3$ |
| Absorption coefficient | 1.776 mm$^{-1}$ |
| F(000) | 1192 |
| Crystal size | 0.42 × 0.34 × 0.19 mm$^3$ |
| Theta range for data collection | 3.16 to 69.44°. |
| Reflections collected | 17640 |
| Independent reflections | 4810 [R(int) = 0.0484] |
| Completeness to theta = 50.43° | 98.0% |
| Absorption correction | Empirical Absorption Correction |
| Max. and min. transmission | 0.7313 and 0.5226 |
| Refinement method | Full-matrix least-squares on F$^2$ |
| Data/restraints/parameters | 4810/6/371 |
| Goodness-of-fit on F$^2$ | 1.029 |
| Final R indices [I > 2sigma(I)] | R1 = 0.0382, wR2 = 0.0988 |
| R indices (all data) | R1 = 0.0432, wR2 = 0.1023 |
| Absolute structure parameter | −0.002(15) |
| Largest diff. peak and hole | 0.341 and −0.190 e · Å$^{-3}$ |

Figure 3:
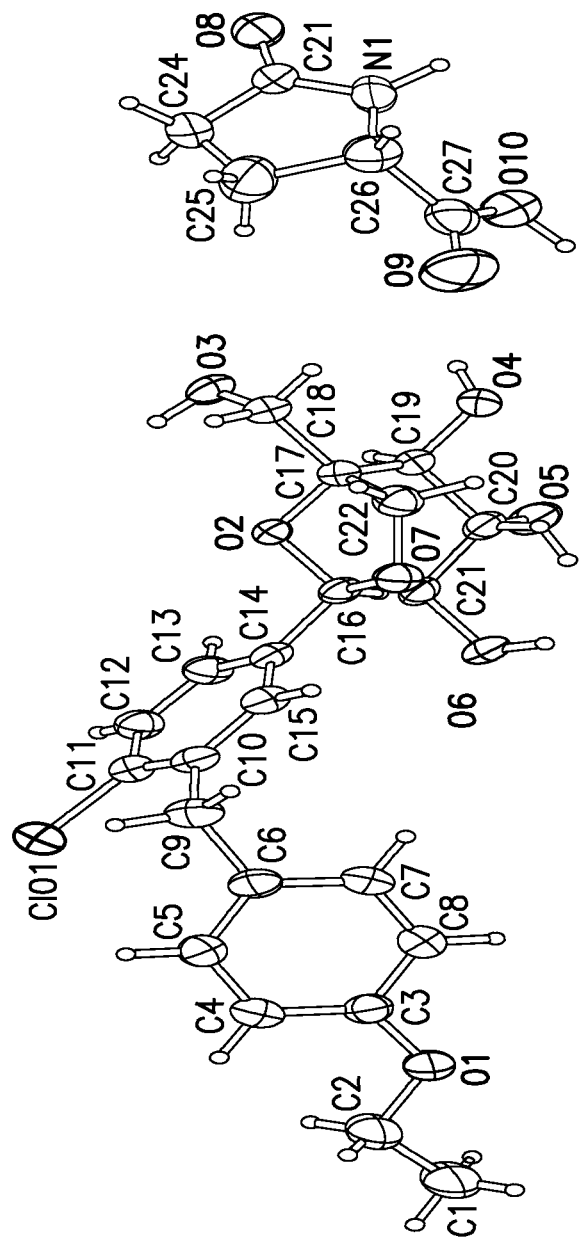
FIG. 3 represents the Ortep drawing of 1·L-PGA cocrystal with ellipsoids drawn at 50% confidence level.

A trial structure was obtained by direct methods. This trial structure refined routinely. Hydrogen positions were calculated wherever possible. The methyl hydrogens were located by difference Fourier techniques and then idealized. The hydrogen parameters were added to the structure factor calculations but were not refined. The shifts calculated in the final cycles of least squares refinement were all less than 0.1 of the corresponding standard deviations. The refined structure was plotted using the SHELXTL plotting package (FIG. 3). The absolute configuration was determined by the method of Flack. See, Flack, H. D., *Acta Crystallogr.*, A39, 876, (1983).

Example 7

(2R,3S,4S)-2,3,4-tris(benzyloxy)-4-((R)-4-((benzyloxy)methyl)-2,2-dimethyl-1,3-dioxolan-4-yl)-1-(4-methylpiperazin-1-yl)butan-1-one (Formula 22 5R diastereomer)

Formula 22

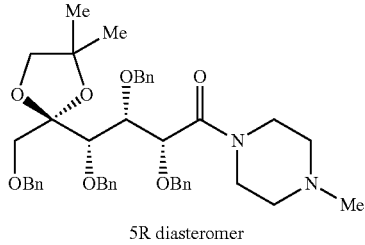

5R diasteromer

A suspension of Formula 22 oxalate prepared via Grignard reagent of formula 21 prepared by Approach B (150.0 g, 188.0 mmol) in methyl tert-butyl ether (1.5 L) was charged with 1N NaOH (405 mL, 405 mmol) and water (405 mL). The resulting mixture was stirred under a nitrogen atmosphere at 40° C. for 30 min to provide a brown solution. The phases were separated, the organic layer was washed with water (500 mL), and then concentrated at 45° C./150 torr to a volume of ca. 450 mL. Cyclohexane (500 mL) was then added, and the mixture was concentrated at atmospheric pressure to a volume of ca. 400 mL (internal temperature 78° C.). Additional cyclohexane (500 mL) was added, and the distillation was repeated to an end volume of ca. 550 mL (internal temperature ca. 83° C.). The solution was then cooled to ca. 40° C. and seed crystals (free base, 500 mg) were added. The resulting light suspension was stirred at 40° C. for ca. 2 h, then was cooled to 12° C. over 4 h and stirred with low agitation (100 rpm) for 18 h. The resulting thick slurry was filtered, the solids were washed with cyclohexane (3×80 mL) and dried under vacuum (30° C./40 torr) to provide free base (115.7 g, 87%) as off-white crystals. The minor diastereomer was not detected by UHPLC. Purity >99.5% (UHPLC-MS). Melting point 87° C.

$^1$H NMR (DMSO-d$_6$, 500 MHz, 25° C.): 7.38-7.19 (m, 20H), 4.78 (d, J=11.4 Hz, 1H), 4.76 (d, J=10.6 Hz, 1H), 4.63 (d, J=11.4 Hz, 1H), 4.62 (d, J=7.17 Hz, 1H), 4.61 (d, J=11.5 Hz, 1H), 4.56 (d, J=12.3 Hz, 1H), 4.53 (d, J=12.3 Hz, 1H), 4.51 (d, J=11.5 Hz, 1H), 4.49 (d, J=11.4 Hz, 1H), 4.18 (d, J=7.17 Hz, 2.87 Hz, 1H), 3.92 (d, J=9.1 Hz, 1H), 3.86 (d, J=2.87 Hz, 1H), 3.66 (d, J=9.1 Hz, 1H), 3.64 (b, 1H), 3.55 (d, J=10.6 Hz, 1H), 3.53-3.44 (b, 2H), 3.47 (d, J=10.6 Hz, 1H), 3.39 (b, 1H), 2.29-2.04 (b, 4H), 2.08 (s, 3H), 1.29 (s, 3H), 1.17 (s, 3H). $^{13}$C NMR (DMSO-d$_6$, 125.8 MHz, 25° C.): 167.1, 138.7, 138.2, 137.9, 137.5, 128.17, 128.15, 128.1, 128.0, 127.8, 127.60, 127.57, 127.43, 127.36, 127.04, 127.01, 108.2, 85.4, 81.3, 78.6, 78.1, 74.3, 73.6, 72.7, 71.7, 71.3, 67.2, 54.5, 54.2, 45.4, 44.6, 41.5, 27.4, 26.0.

HRMS: (ESI$^+$) Calcd for C$_{43}$H$_{53}$N$_2$O$_7$ (M+H)$^+$: 709.38473, Found: 709.38407.

Throughout this application, various publications are referenced. The disclosures of these publications in their entireties are hereby incorporated by reference into this application for all purposes.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification including the examples be considered as exemplary only, with a true scope and spirit of the invention being indicated by the following claims.

What is claimed is:
1. A compound of formula 27

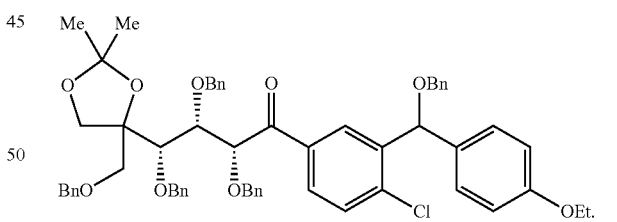

2. A method for preparing a compound of formula 1

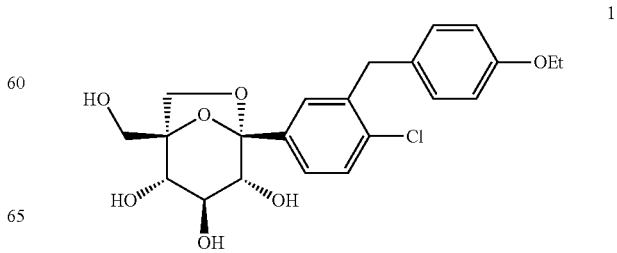

comprising treating a compound of formula 28a/b

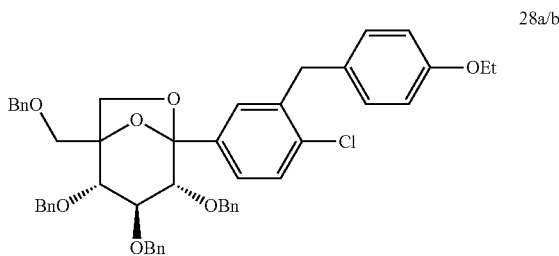 [SMILES: CCOc1ccc(Cc2cc(C34OCC(COCc5ccccc5)(O3)[C@@H](OCc3ccccc3)[C@H](OCc3ccccc3)[C@H]4OCc3ccccc3)ccc2Cl)cc1]

with a hydrogenolysis agent and an acid, and wherein the compound is treated using acidic conditions resulting in complete conversion to the compound of formula 1.

3. The method of claim 2 wherein the hydrogenolysis agent is hydrogen in the presence of palladium.

4. A method for preparing a compound of formula 1

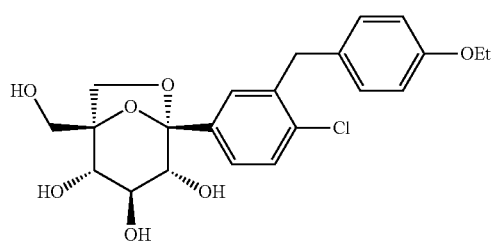

comprising treating a compound of formula 28a/b

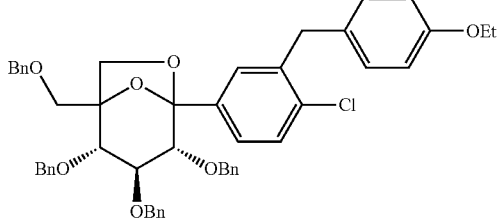

with a hydrogenolysis agent; and further comprising preparing the compound of formula 28a/b by reducing a compound of formula 27

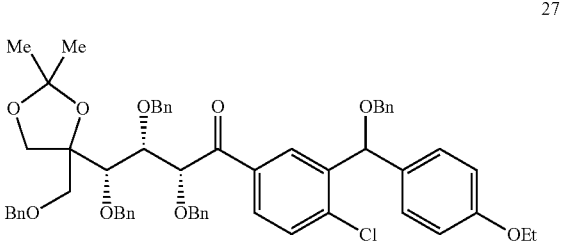 [SMILES: CCOc1ccc(C(OCc2ccccc2)c2cc(C(=O)[C@H](OCc3ccccc3)[C@@H](OCc3ccccc3)[C@H](OCc3ccccc3)C3(COCc4ccccc4)COC(C)(C)O3)ccc2Cl)cc1]

with an acid and a reducing agent.

5. The method of claim 4 wherein the acid is trifluoroacetic acid and the reducing agent is triethylsilane.

6. The method of claim 4 further comprising preparing the compound of formula 27 by reacting the compound of formula 26e

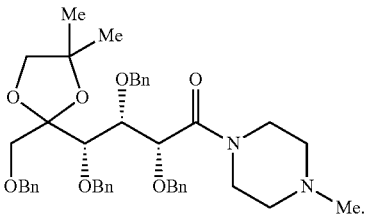

with a halogen metal exchange agent and a compound of formula 22

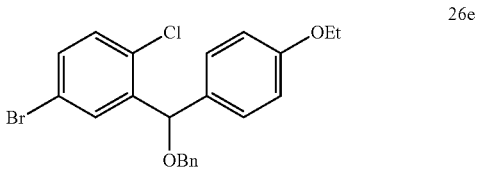 [SMILES: CCOc1ccc(C(OCc2ccccc2)c2cc(Br)ccc2Cl)cc1]

7. The method of claim 6 wherein the halogen metal exchange agent is n-butyllithium or hexyllithium.

* * * * *